United States Patent [19]

Brown

[11] 4,203,932
[45] May 20, 1980

[54] PHOSPHORYL HYDRAZINES

[75] Inventor: Michael J. Brown, Randolph, N.J.

[73] Assignee: GAF Corporation, New York, N.Y.

[21] Appl. No.: 16,132

[22] Filed: Mar. 1, 1979

[51] Int. Cl.² ..................... A01N 9/36; C07F 9/24; C07F 9/22

[52] U.S. Cl. .............. 260/923; 260/551 P; 424/211; 424/220

[58] Field of Search ............. 260/923, 551 P; 424/211, 220

[56] References Cited

U.S. PATENT DOCUMENTS

| | | | |
|---|---|---|---|
| 2,855,423 | 10/1958 | Blair | 260/923 |
| 2,906,770 | 9/1959 | Debo | 260/923 |

FOREIGN PATENT DOCUMENTS 626632  8/1961  Canada ..................... 260/923

Primary Examiner—Anton H. Sutto

Attorney, Agent, or Firm—Walter C. Kehm; Walter Katz

[57] ABSTRACT

Compounds and compositions of the formula:

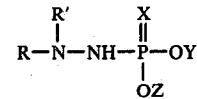

where
 R and R' are both alkyl, $C_1$–$C_3$; or
 R is acyl, $C_2$–$C_6$ and R' is alkyl, $C_1$–$C_6$ or hydrogen; or
 R is carbalkoxyalkyl, $C_2$–$C_6$ and R' is hydrogen;
 X is oxygen or sulfur; and;
 Y and Z are both alkyl, $C_1$–$C_6$; are described herein.

The compositions exhibit insecticidal and miticidal activity.

2 Claims, No Drawings

PHOSPHORYL HYDRAZINES

BACKGROUND OF THE INVENTION

1. Field of the Invention

This invention relates to phosphoryl hydrazines, and particularly to novel compounds and compositions, which exhibit insecticidal and miticidal activity, and to methods of combatting pests with these materials.

2. Description of the Prior Art

Compounds in the substituted phosphoryl hydrazine series have been reported in the literature. For example, in the articles referred to in Chemical Abstracts 55,9320g; 54,7051f; 52,4920a; 50,2415h and 53,3113; in the U.S. Pat. No. 2,906,770 and German Pat. No. 1,011,432, there are disclosed related hydrazine compounds and their synthesis. However, none of these prior art compounds have the essential structural features of the novel compounds of this invention, which, significantly, provide useful agricultural insecticidal and miticidal activity.

SUMMARY OF THE INVENTION

Compounds and compositions of the formula:

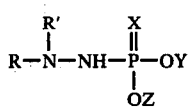

where
R and R' are both alkyl, $C_1$–$C_3$; or
R is acyl, $C_2$–$C_6$ and R' is alkyl, $C_1$–$C_6$ or hydrogen; or
R is carbalkoxyalkyl, $C_2$–$C_6$ and R' is hydrogen;
X is oxygen or sulfur; and
Y and Z are both alkyl, $C_1$–$C_6$; are described herein.

The compositions exhibit insecticidal and miticidal activity.

DESCRIPTION OF THE INVENTION

The novel compounds of the invention may be prepared by reaction between a suitable substituted hydrazine and a dialkylphosphite, using the solid-liquid phase transfer catalysis technique described by Zwierzak and Sulewska in Synthesis (1976), p. 835 for related compounds. The starting dialkylphosphite material usually is available commercially, e.g. from the Aldrich Chemical Co., or can be made by the method given in Chemical Abstracts 55,14308d.

Alternatively, the compounds herein may be synthesized by reaction between a substituted hydrazine and an chlorodialkylphosphate under classical homogeneous solution conditions, in the presence of an organic base, as described by Pelchowicz in the J. Chem. Soc. (1961), p. 238, for related compounds. This compound usually is available commercially.

The substituted hydrazine starting material may be used in the form of its hydrochloride salt or as the free base in the phase transfer catalysis method while under homogeneous solution conditions only the free base is used. The chloro derivative of the dialkylphosphite also may be used in the phase transfer technique instead of the dialkylphosphite, and, is probably formed "in situ" during the catalyzed reaction. The corresponding thiophosphite and chlorothiophosphate compounds are used as starting materials where the thiophosphoryl hydrazines are the desired products.

Under the general phase transfer reaction conditions, condensation can occur at either nitrogen of the hydrazine starting material. The nature of the reaction depended upon the size of the substituent on the hydrazine used. Phenyl phosphoryl or N-aminoheterocyclic substituted hydrazines for example, reacted to give phosphoryl condensation on the unsubstituted nitrogen, e.g. the compound 1-phenyl-2-diethoxyphosphoryl hydrazine,

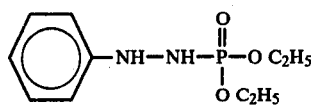

Isopropyl hydrazine, however, apparently underwent an alkylation reaction with dimethyl phosphite under the phase-transfer reaction conditions since the chief product was N-methylated.

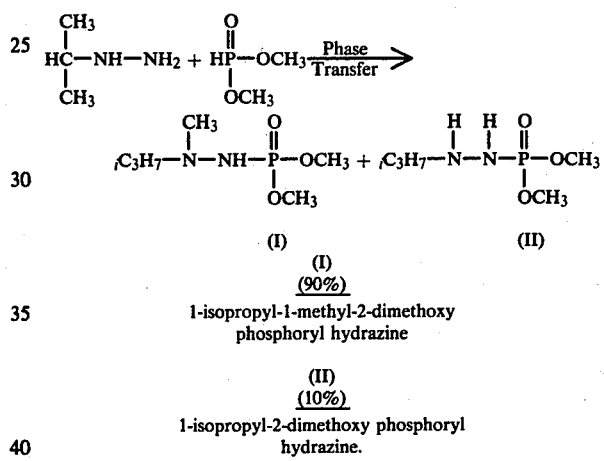

(I)
(90%)
1-isopropyl-1-methyl-2-dimethoxy phosphoryl hydrazine (II)
(10%)
1-isopropyl-2-dimethoxy phosphoryl hydrazine.

A similar result was obtained using chlorodimethoxyphosphorothiate.

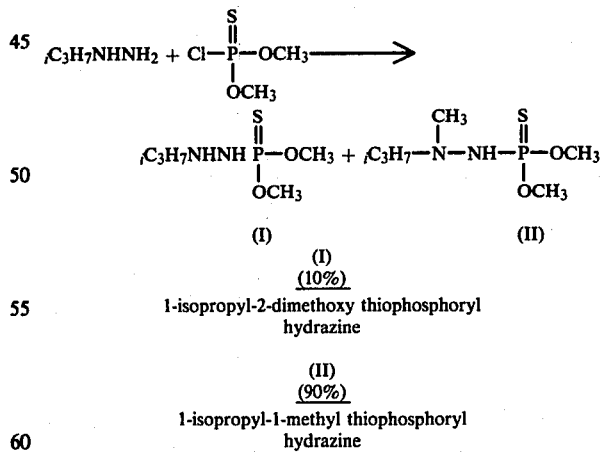

(I)
(10%)
1-isopropyl-2-dimethoxy thiophosphoryl hydrazine (II)
(90%)
1-isopropyl-1-methyl thiophosphoryl hydrazine Compounds in which R' is a substituent other than hydrogen, i.e. alkyl or acyl, are made by conventional alkylation or acylation of the parent compound, in which R' is hydrogen.

The preferred compounds of the invention are those in which both R and R' are alkyl $C_1$–$C_3$; e.g. methyl, ethyl, isopropyl, etc.; R is alkyl $C_1$–$C_6$ and R' is acyl; or R is carbalkoxyalkyl, $C_2$-$C_6$ and R' is hydrogen; X is oxygen or sulfur; and Z is alkyl, $C_1$-$C_6$, e.g. methyl, ethyl, etc.

The invention compounds of the formula are useful as insecticides or miticides, and are most conveniently used as such when formulated into the compositions. In another aspect, therefore, the invention provides insecticidal and miticidal compositions which comprise as an active ingredient compound of the formula in association with agriculturally and horticulturally acceptable diluent or carrier materials.

In this aspect of the invention the active ingredient is selected from among the specifically named compounds of the invention set out hereinabove.

The compositions are for use in agriculture or horticulture but the type of composition used in any instance will depend upon the particular purpose for which it is to be used.

In use, the invention compounds or compositions may be used to combat insects or mites in a variety of ways. Thus the insects themselves, or the locus of the insects or the habitat of the insects is treated with a compound or a composition according to the invention.

The invention also provides a method of treating plants to render them less susceptible to damage by insects, which comprises treating the plants, or the seeds, corns, bulbs, tubers, rhizomes or other propagative parts of the plants, or the medium in which the plants are growing with a compound or composition according to the invention.

The composition of the present invention may be applied to the soil of the insect susceptible plants on the site at a rate of about 1 pound or less to about 25 pounds per acre, or as a foliar dust or spray at concentrations of about 31 to 260 ppm, depending on various circumstances of the susceptibility of the insects, the weather, the stage of growth and various other factors. As a dust, it is more practical to extend it with diluents such as bentonite, chalk, clay, diatomaceous earth, fullers earth, mica, ground slate or any of the other usual carriers for agricultrual chemicals. As a spray, it may be incorporated into water as a solution. The higher molecular weight compounds may be dissolved first in a solvent, such as an alcohol, or a petroleum fraction, such as isoparaffinic hydrocarbons, naphtha or kerosene, which may be dissolved in a suitable solvent and fogged or sprayed without water. Usually it is desirable to incorporate emulsifying agents and other wetting agents to insure complete contact with the insect.

EXAMPLE 1

1-Acetyl-2-Diethoxyphosphoryl Hydrazine

Diethylphosphorohydrazidate (5.3 g) and triethylamine (13 ml) were dissolved in dichloromethane (15 ml). To this solution was added dropwise with stirring and cooling a solution of acetyl chloride (7.4 g) in dichloromethane (15 ml). The mixture was then stirred at ambient temperature and then filtered to remove the triethylamine hydrochloride after the addition of 50 ml of anhydrous diethylether. The filtrates were stripped on a rotary evaporator to yield a red-brown oil which was distilled under high vacuum to give a pale yellow liquid, b.p. 180° C./1 mm, identified as the product.

EXAMPLE 2

1-Acetyl-2-Dimethoxyphosphoryl Hydrazines

This compound was prepared in a similar manner to the compound of Example 1, but using dimethylphosphorohydrazidate instead of diethylphosphorohydrazidate. The product distilled at 95°–115°/0.03 mm.

EXAMPLE 3

1-Acetyl-2-Diisopropoxyphosphoryl Hydrazine

This compound was prepared in a similar manner to the compound of Example 1, but using diisopropylphosphorohydrazidate instead of diethylphosphorohydrazidate, and pyridine in place of triethylamine. The product distilled at 130°–140° C./0.07 mm.

EXAMPLE 4

1-Methyl-1-Isopropyl-2-Dimethoxythiophosphoryl Hydrazine

A mixture of isopropylhydrazine (7.42 g, 0.1 mole), potassium carbonate (20.73 g, 0.15 mole) and triethylbenzyl ammonium chloride (0.3 g, 0.0013 mole was stirred vigorously at reflux with dichloromethane (100 ml) and carbon tetrachloride (60 ml) for 30 minutes. A solution of dimethylchlorothiophosphate (16.6 g, 0.1 mole) in dichloromethane (20 ml) was then added dropwise to this refluxing mixture and the mixture stirred and refluxed for an additional 20 hours. The mixture was then filtered and the filtrate dried over anhydrous magnesium sulfate. The dried filtrate, then was evaporated down to a viscous oil which was subjected to high vacuum for 2 or 3 hours to yield 6.5 g of a thick yellow oil, $n_D^{25°} = 1.5132$, identified as the product by NMR, IR and mass spectroscopy.

EXAMPLE 5

1-Acetyl-1-Methyl-2-Diethoxyphosphoryl Hydrazine

A mixture of 1-acetyl-1-methyl hydrazine (7.84 g., 0.09 mole), potassium carbonate (18.44 g., 0.13 mole) and triethylbenzyl ammonium chloride (0.2 g,) was stirred vigorously at reflux with dichloromethane (90 ml) and carbon tetrachloride (55 ml) for 30 minutes. A solution of diethylphosphite (12.29 g, 0.09 mole) in dichloromethane (18 ml) was then added dropwise to this refluxing mixture and the mixture stirred and refluxed for an additional 20 hours. The mixture was then filtered and the filtrate dried over anhydrous magnesium sulfate. The dried filtrate, then was evaporated down to an oil which was subjected to high vacuum for 2 or 3 hours to yield a liquid product, characterized by proton NMR, infra-red and mass spectroscopy as the subject compound.

EXAMPLE 6

1-Carbomethoxymethyl-2-Diethoxyphosphoryl Hydrazine

This compound was synthesized in a similar manner to the compound of Example 5, except that methylhydrazinoacetate hydrochloride was used in place of 1-acetyl-1-methyl hydrazine and diethylphosphite was used in place of dimethylphosphite. A colorless oil was obtained which was subsequently distilled at 115° C./0.05 mm. to yield the desired product, $n_D^{27} = 1.4342$.

TABLE I

COMPOUNDS OF THE INVENTION HAVING THE FORMULA GIVEN ABOVE.

| No. | R | R' | R'' | X | Y | Z | BP(MP or $n_D$) |
|---|---|---|---|---|---|---|---|
| 1 | H | H | $CH_3$ | O | $C_2H_5$ | $C_2H_5$ | 80°/0.46 mm |
| 2 | $CH_3CO-$ | H | $CH_3$ | O | $C_2H_5$ | $C_2H_5$ | 112°/0.05 mm |
| 3 | H | H | $n-C_3H_7$ | O | $CH_3$ | $CH_3$ | 85°–90°/0.12 mm |
| 4 | $CH_3CO-$ | H | $n-C_3H_7$ | O | $CH_3$ | $CH_3$ | 1.4542 $^{24°}$ |
| 5 | $CH_3CO-$ | $CH_3$ | H | O | $C_2H_5$ | $C_2H_5$ | — |
| 6 | $CH_3CO-$ | H | H | O | $CH_3$ | $CH_3$ | 95/0.3 mm |
| 7 | $H_2NCO-$ | $CH_3$ | $CH_3$ | O | $C_2H_5$ | $C_2H_5$ | 1,4396 $^{22°}$ |
| 8(A) | $CF_3CO-$ | H | H | O | $C_2H_5$ | $C_2H_5$ | 115°/0.1 mm |
| 9 | $n-C_3H_7CO-$ | H | H | O | $C_2H_5$ | $C_2H_5$ | mp. 125°–30° |
| 10 | $(C_2H_5O)_2P(O)-NH-NH-CH_2CO-$ | H | H | O | $C_2H_5$ | $C_2H_5$ | 110°/0.5 mm |
| 11(B) | $C_6H_5-CH_2-$ | H | H | O | $CH_3$ | $CH_3$ | 1,5302 $^{25°}$ |
| 12 | $C_6H_5-N=C(Cl)(CH_3)-$ | H | H | O | $C_2H_5$ | $C_2H_5$ | mp. 69°–74° |
| 13 | (2-oxopyrrolidin-1-yl)-$CH_2-$ | H | H | O | $C_2H_5$ | $C_2H_5$ | 1.4988 $^{22°}$ |
| 14 | $CH_3OC(O)CH_2-$ | H | H | O | $C_2H_5$ | $C_2H_5$ | 1.4342 $^{27°}$ |
| 15 | $CH_3-$ | $CH_3$ | H | O | $CH_3$ | $CH_3$ | mp 32°–5° |
| 16 | $CH_3OC(O)CH_2-$ | $CH_3$ | H | O | $C_2H_5$ | $C_2H_5$ | 1.4470 $^{24°}$ |
| 17 | $(CH_3)_2CH-$ | $CH_3$ | H | O | $CH_3$ | $CH_3$ | 88°/0.02 mm |
| 18 | $(CH_3)_2CH-$ | $CH_3$ | H | S | $CH_3$ | $CH_3$ | 1.5132 $^{25°}$ |
| 19 | H | H | $n-C_4H_9$ | O | $CH_3$ | $CH_3$ | 1.4524 $^{25°}$ |
| 20 | H | H | H | O | $CH_3$ | $CH_3$ | 1.4677 $^{25°}$ |
| 21 | H | H | H | O | $C_2H_5$ | $C_2H_5$ | 55°/0.1 mm. |
| 22 | $CH_3CO-$ | H | H | O | $C_2H_5$ | $C_2H_5$ | 180°/1 mm |
| 23 | H | H | H | O | $i-C_3H_7$ | $i-C_3H_7$ | 1.4405 $^{25°}$ |
| 24 | $CH_3CO-$ | H | H | O | $i-C_3H_7$ | $i-C_3H_7$ | 130°–40°/0.07 mm |
| 25 | H | H | H | O | $n-C_4H_9$ | $n-C_4H_9$ | — |
| 26 | $CH_3CO-$ | H | H | O | $n-C_4H_9$ | $n-C_4H_9$ | 1.4592 $^{16°}$ |
| 27 | $C_2H_5O-P(O)(OH)-$ | H | H | O | H | $C_2H_5$ | 1.4361 $^{22°}$ |
| 28 | $C_2H_5O-P(O)(OC_2H_5)-C_2H_5$ | H | H | O | $C_2H_5$ | $C_2H_5$ | mp. 87°–91° |
| 29 | $C_6H_5-$ | H | H | O | $C_2H_5$ | $C_2H_5$ | mp. 100°–2° (d) |
| 30 | $C_6H_5-$ | $CH_3CO-$ | H | O | $C_2H_5$ | $C_2H_5$ | 1.5098 $^{24°}$ |
| 31 | 2,?-dichlorophenyl- | H | H | O | $CH_3$ | $CH_3$ | mp. 133°–5° |

TABLE I-continued

COMPOUNDS OF THE INVENTION HAVING THE FORMULA GIVEN ABOVE.

$$\begin{array}{c} R' \;\; R'' \;\; X \\ | \;\;\; | \;\;\; \| \\ R-N-N-P-OY \\ | \\ OZ \end{array}$$

| No. | R | R' | R'' | X | Y | Z | BP(mp or $n_D$) |
|---|---|---|---|---|---|---|---|
| 32 | CH$_3$-C$_6$H$_4$- | H | H | O | CH$_3$ | CH$_3$ | mp. 99°–100° |
| 33 | (CF$_3$)(NO$_2$)$_2$C$_6$H$_2$- | H | H | O | C$_2$H$_5$ | C$_2$H$_5$ | — |

| No. | R—N—R' | R'' | X | Y | Z | BP(mp or $n_D$) |
|---|---|---|---|---|---|---|
| 34 | morpholino | H | O | CH$_3$ | CH$_3$ | mp. 135°–45° (d) |
| 35 | piperidino | H | O | CH$_3$ | CH$_3$ | 1.4788 $^{25°}$ |
| 36 | hexahydroazepin-1-yl | H | O | CH$_3$ | CH$_3$ | 1.4968 $^{25°}$ |
| 37 | (CH$_3$)$_3$N$^+$—I$^-$·H$_2$O | H | O | CH$_3$ | CH$_3$ | 1.4903 $^{23°}$ |

Note(A): CF$_3$CONHNHP(O)(OC$_2$H$_5$)$_2$ · CF$_3$COOH

Note(B): An isometric mixture of:

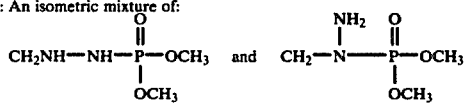

$$CH_2NH-NH-P(O)(OCH_3)-OCH_3 \quad \text{and} \quad CH_2-N(NH_2)-P(O)(OCH_3)-OCH_3$$

TABLE II

PRIMARY INSECTICIDAL/MITICIDAL ACTIVITY*

| | Compound No. in Table I | | | | | | | | | | | |
|---|---|---|---|---|---|---|---|---|---|---|---|---|
| | 5 | | 6 | | 14 | | 18 | | 22 | | 24 | |
| Insect or Mite | Ad. | Im. | Ad. | Im. | Ad. | Im. | Ad. | Im. | Ad. | Im. | Ad. | Im. |
| Mex. Bean Beetle | | 3 | | 1 | | 9 | | 10 | | 6 | | 1 |
| Southern Armyworm | | 0 | | 0 | | 8 | | 0 | | 3 | | 0 |
| 2-Spotted Mite | 5 | 1 | 9 | 9 | 1 | 0 | 8 | 7 | 5 | 0 | 0 | 0 |
| Bean Aphid | 10 | | 9 | | 8 | | 1 | | 10 | | 8 | |

*Tests run with foliage spray at 260 ppm. An additional soil application at 25 lbs per acre was used for the 2-spotted mite and bean aphid tests. The results were rated as 0 (no kill) to 10 (complete kill);
Ad = adult;
Im = immature.

What is claimed is:

1. Compounds having the formula:

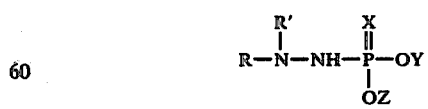

where
R is carbalkoxyalkyl, C$_2$–C$_6$ and
R' is hydrogen;
X is oxygen or sulfur; and,
Y and Z are both alkyl, C$_1$–C$_6$.

2. A compound according to claim 1 which is 1-carbomethoxymethyl-2-diethoxy phosphoryl hydrazine.

* * * * *